US005866553A

United States Patent [19]
Donnelly et al.

[11] Patent Number: 5,866,553
[45] Date of Patent: Feb. 2, 1999

[54] POLYNUCLEOTIDE VACCINE FOR PAPILLOMAVIRUS

[75] Inventors: John J. Donnelly, Havertown; Margaret A. Liu, Rosemont; Douglas Martinez, Lansdale; Donna L. Montgomery, Chalfont, all of Pa.

[73] Assignee: Merck & Co., Inc., Rahway, N.J.

[21] Appl. No.: 750,810

[22] PCT Filed: Jun. 1, 1995

[86] PCT No.: PCT/US95/06915

§ 371 Date: Dec. 17, 1996

§ 102(e) Date: Dec. 17, 1996

[87] PCT Pub. No.: WO96/00583

PCT Pub. Date: Jan. 11, 1996

Related U.S. Application Data

[63] Continuation-in-part of Ser. No. 268,424, Jun. 30, 1994, abandoned.

[51] Int. Cl.$^6$ ................................................ A01N 43/04
[52] U.S. Cl. ..................... 514/44; 435/320.1; 435/172.3; 536/23.1
[58] Field of Search ............................ 514/44; 536/23.1, 536/23.5; 435/172.3

[56] References Cited

U.S. PATENT DOCUMENTS

| | | | |
|---|---|---|---|
| 4,497,796 | 2/1985 | Salser et al. | 424/95 |
| 5,415,995 | 5/1995 | Schoolnik et al. | 435/7.1 |
| 5,576,206 | 11/1996 | Schlegel | 435/240.2 |
| 5,593,972 | 1/1997 | Weiner et al. | 514/44 |

FOREIGN PATENT DOCUMENTS

| | | |
|---|---|---|
| 0 586 076 A2 | 7/1993 | European Pat. Off. . |
| WO 86/05816 | 10/1986 | WIPO . |
| WO 90/11092 | 10/1990 | WIPO . |
| WO 93/02184 | 2/1993 | WIPO . |
| WO 94/05792 | 3/1994 | WIPO . |

OTHER PUBLICATIONS

Lin et al. Progression from Papilloma to Carcinoma is Accompanied by Changes in Antibody Response to Papillomavirus Proteins. Journal of Virology, vol. 67, No. 1, pp. 382–389, Jan. 1993.
Lin et al. Cottontail Rabbit Papillomavirus L1 Protein–Based Vaccines: Protection is Achieved Only with a Full–Length, Nondenatured Product. Journal of Virology, vol. 67, No. 7, pp. 4154–4162, Jul. 1993.
Meyers et al. Identification of Three Transforming Proteins Encoded by Cottontail Rabbit Papillomavirus. Journal of Virology, vol. 66, No. 3, pp. 1655–1664, Mar. 1992.
Orkin et al. Report and recommendations of the panel to assess the NIH investment in research on gene therapy, Issued by the National Institutes of Health, Dec. 7, 1995.
Strayer, D. S. The viruses don't always read the books–engineered vaccines and gene–therapy using viral vectors. Laboratory Investigation, vol. 71, No. 3, pp. 319–323, Sep. 1994.
Cason, J. Papilloma virus vaccines– current status. Clinical Immunotherapeutics, vol. 1, No. 4, pp. 293–306, Apr. 1994.
Browne, et al., "Analysis of the L1 Gene Product of Human Papillomavirus Type 16 by Expression . . . ", J. Gen. Virol., (1988), vol. 69, pp. 1263–1273.
Doorbar, et al., "Identification of Proteins Encoded by the L1 and L2 Open Reading Frames ofHuman Papillomavirus 1a", J. of Virol., Sep. 1987, vol. 67, No. 9, pp. 2793–2799.
Hagenese, et al., "Self–Assembly of Human Papillomavirus Type 1 Capsids by Expression of the L1 Protein Alone or by Coexpression . . . ", J. of Virol., Jan. 1993, vol. 67, No. 1, pp. 315–322.
Kirnbauer, "Papillomavirus L1 major capsid protein self–assembles into virus–like particles that are highly immunogenic", Proc. Natl. Acad. Sci., Vo. 89, pp. 12180–12184, Dec. 1992.
LeCann, et al., "Self–assembly of human papillomavirus type 16 capsids by expression of the L1 protein in insect cells", FEMS Microbiology Letters, 117, (1994), pp. 269–274.
Lin, et al., "Effective Vaccination against Papillomavirus Development by immunization with L1 or L2 Structural Protein of Cottontail Rabbit Papillomavirus", Virology, vol. 187, (1992), pp. 612–619.
Rose, et al., "Expression of Human Papillomavirus Type 11 L1 Protein in Insect Cells: In Vivo and In Vitro Assembly of Viruslike Particles", J. of Virol., Apr. 1993, pp. 1936–1944.
Steele, et al., "Humoral Assays of Human Sera to Disrupted and Nondisrupted Epitopes of Human Papillomavirus Type 1", Virology., vol. 174, (1990) pp. 388–398.
Strike, et al., "Expression in *Escherichia coli* of Seven DNA Fragments Comprising the Complete L1 and L2 Open . . . ", J. Gen. Virol. (1989) vol. 70, pp. 543–555.
Zhou, et al., "Synthesis and assembly of infectious bovine papillomavirus particles in vitro", J. Gen. Virol., (1993), vol. 74, pp. 763–768.
Zhou, et al., "Increased antibody responses to human papillomavirus type 16 L1 protein expressed by recombinant", J. Gen. Virol., (1990) vol. 71, pp. 2185–2190.
Wolfe, et al., "An Early History of Gene Transfer and Therapy", Human Gene Therapy, vol. 5, pp. 467–480 (1994).
Ulmer , et al., "The Generation of Protective Humoral and Cell–Mediated Immunity of Polynucleotide Vaccines", FASED Journal, No. 4, 5 p. A748 (1994).
Wolff, et al., "Direct Gene Transfer into Mouse Muscle in Vivo", Science, vol. 247, pp. 1464–1468 (1990).
Zhou, et al., "Expression of Vaccinia Recombinant HPV 16 L1 and L2 ORF Proteins in Epithelial Cells is Sufficient for Assembly of HPV Virion–like Particles", Virology, vol. 185, (1991), pp. 251–257.
Ulmer, et al., "Heterologous Protection Against Influenza by Injection of DNA Encoding a Viral Protein", Science, vol. 259, pp. 1745–1749 (1993).

Primary Examiner—Jasemine C. Chambers
Assistant Examiner—Deborah J. R. Clark
Attorney, Agent, or Firm—Joanne M. Giesser; Jack L. Tribble

[57] ABSTRACT

DNA constructs encoding papilloma virus gene products, capable of being expressed upon direct introduction into animal tissues, are novel prophylactic pharmaceuticals which can provide immune protection against infection by papilloma virus.

4 Claims, 7 Drawing Sheets

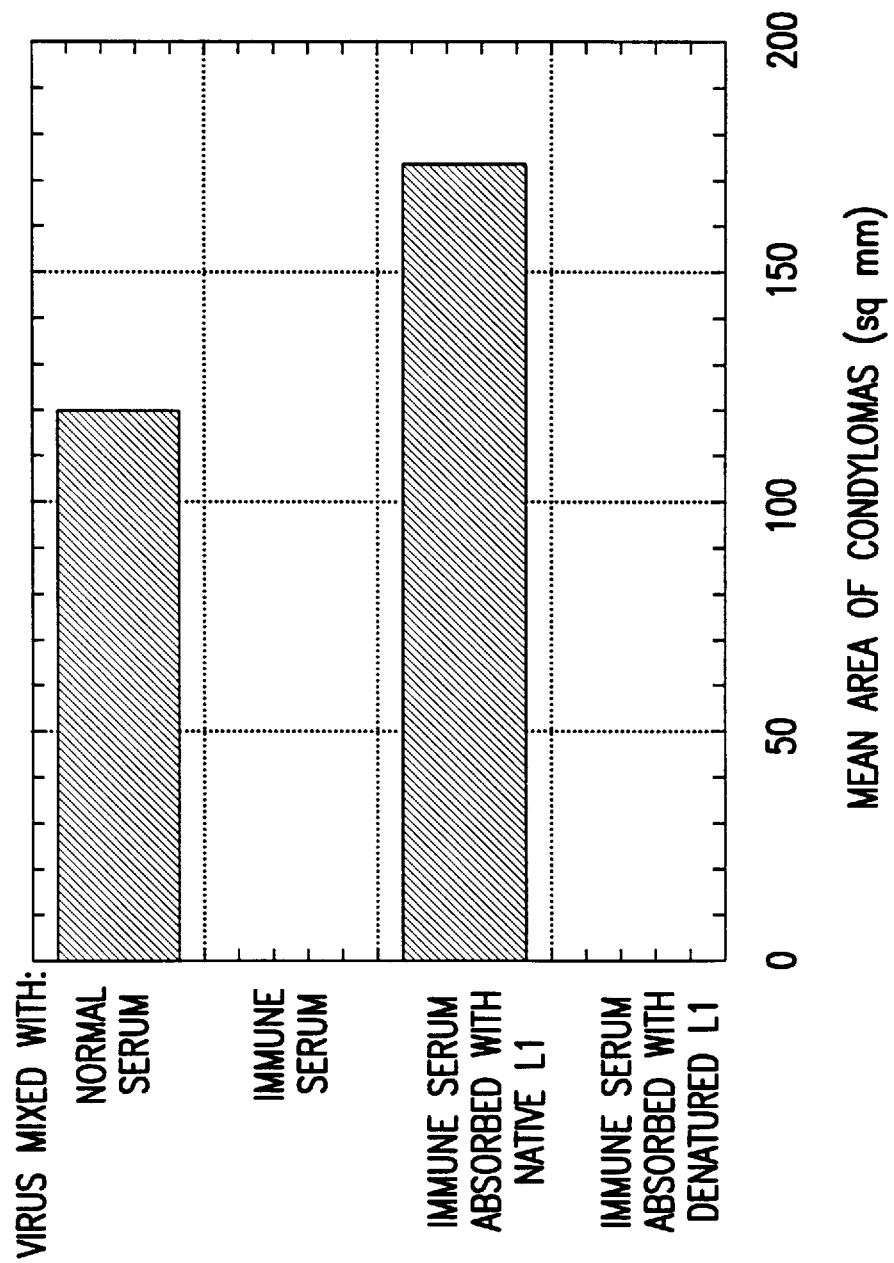

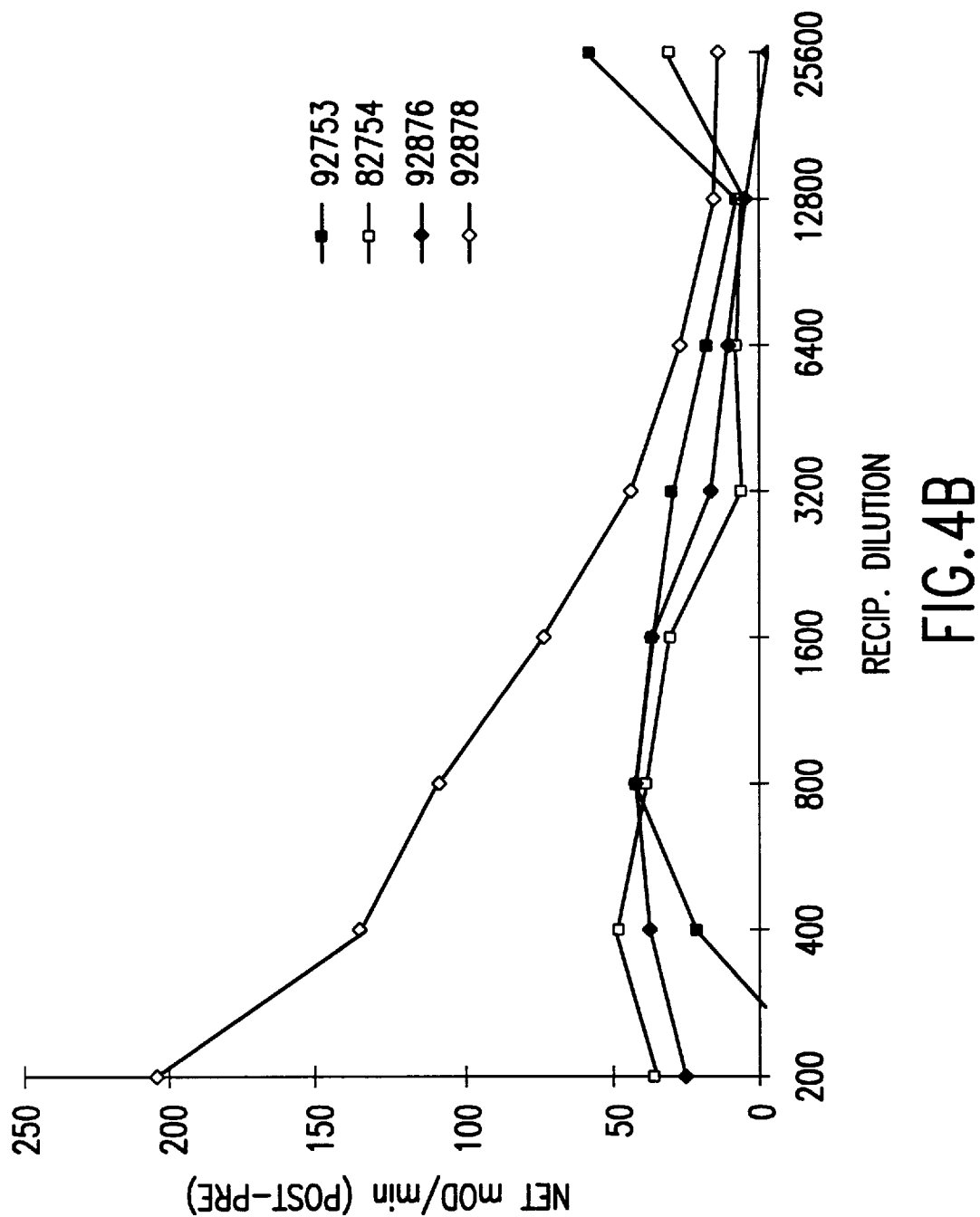

| IMMUNOGEN | VIRUS CHALLENGE DILUTION | NUMBER OF SITES POSITIVE | NUMBER OF SITES CHALLENGED | TIME POST CHALLENGE |
|---|---|---|---|---|
| L1 DNA OR L1+L2 DNA | 1:2 1:12 | 1 0 | 30 30 | 10 WEEKS |
| L2 DNA OR CONTROL DNA | 1:2 1:12 | 27 24 | 27 27 | 10 WEEKS |

FIG.5

POLYNUCLEOTIDE VACCINE FOR PAPILLOMAVIRUS

CROSS-RELATED TO OTHER APPLICATION

This is a continuation-in-part of U.S. Ser. No. 08/268,424 filed Jun. 30, 1994, now abandoned.

FIELD OF THE INVENTION

This invention relates to the production and use of a novel pharmaceutical product: a nucleic acid which, when directly introduced into living vertebrate tissue, induces an immune response which specifically recognizes papilloma virus.

BACKGROUND OF THE INVENTION

Papilloma virus (PV) infections occur in a variety of animals, including humans, sheep, dogs, cats, rabbits, monkeys, snakes and cattle. Papilloma viruses infect epithelial cells, generally inducing benign epithelial or fibroepithelial tumors at the site of infection. Papilloma viruses are species specific infective agents; e.g., a human papillomavirus generally does not infect a nonhuman animal.

Papilloma viruses may be classified into distinct groups based on the host that they infect. Human papilloma viruses (HPV) are further classified into more than 60 types based on DNA sequence homology (for a review, see Papilloma Viruses and Human Cancer, H. Pfister (ed.), CRC Press, Inc., 1990). Papilloma virus infections appear to induce type-specific immunogenic responses in that a neutralizing immunity to infection to one type of papilloma virus may not confer immunity against another type of papilloma virus.

In humans, different HPV types cause distinct diseases. HPV types 1,2, 3, 4, 7, 10 and 26–29 cause benign warts in both normal and immunocompromised individuals. HPV types 5, 9, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital tract. HPV types 16 and 18 cause epithelial dysplasia of the genital tract and are associated with the majority of in situ and invasive carcinomas of the cervix, vagina, vulva and anal canal.

Immunological studies in animal systems have shown that the production of neutralizing antibodies to papilloma virus antigens prevents infection with the homologous virus. The development of effective human papilloma virus vaccines has been slowed by the inability to cultivate papilloma viruses in vitro. The development of an effective HPV vaccine has been particularly slowed by the absence of a suitable animal host for the direct study of HPV.

Neutralization of papilloma virus by antibodies appears to be type-specific and dependent upon conformational epitopes on the surface of the virus.

Papilloma viruses are small (50–60 nm), nonenveloped, icosahedral DNA viruses that encode for early and late genes. The open reading frames (ORFs) of the virus genomes are designated E1 to E7 and L1 and L2, where "E" denotes early and "L" denotes late. L1 and L2 encode virus capsid proteins. E1 to E3 and E5 to E7 are associated with functions such as viral replication and transformation.

The L1 protein is the major capsid protein and has a molecular weight of 55–60K. L2 protein is a minor capsid protein which has a predicted molecular weight of approximately 55K and an apparent molecular weight of 75–100K as determined by polyacrylamide gel electrophoresis. Electron microscopic and immunologic data suggest that most of the L2 protein is internal to the L1 protein. The L2 proteins are highly conserved among different papilloma viruses, especially the 10 basic amino acids at the C-terminus. The L1 ORF is highly conserved among different papilloma viruses.

The L1 and L2 genes have been used to generate recombinant proteins for potential use in the prevention and treatment of papilloma virus infections. Zhou et al. cloned HPV type 16 L1 and L2 genes into a vaccinia virus vector and infected CV-1 mammalian cells with the recombinant vector to produce virus-like particles (VLP). These studies were interpreted as establishing that the expression of both HPV type 16 L1 and L2 proteins in epithelial cells is necessary and sufficient to allow assembly of VLP. The expression of L1 protein alone or L2 protein alone or double infection of cells with single recombinant vaccinia virus vectors containing L1 and L2 genes did not produce particles.

Bacterially-derived recombinant bovine papilloma virus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV16 L1 or HPV16 L2 ORF have been used to infect insect SF9 cells and produce recombinant L1 and L2 proteins. Western blot analyses showed that the baculovirus-derived L1 and L2 proteins reacted with antibody to HPV16. The production of HPV 16 L1 and HPV16 L2 proteins by recombinant strains of *Saccharomyces cerevisiae* has also been demonstrated.

Since cytotoxic T-lymphocytes (CTLs) in both mice and humans are capable of recognizing epitopes derived from conserved internal viral proteins and are thought to be important in the immune response against viruses, efforts have been directed towards the development of CTL vaccines capable of providing heterologous protection against different viral strains.

It is known that $CD8^+$CTLs kill virally-infected cells when their T cell receptors recognize viral peptides associated with MHC class I molecules. These peptides are derived from endogenously synthesized viral proteins, regardless of the protein's location or function within the virus. Thus, by recognition of epitopes from conserved viral proteins, CTLs may provide cross-strain protection. Peptides capable of associating with MHC class I for CTL recognition originate from proteins that are present in or pass through the cytoplasm or endoplasmic reticulum. Therefore, in general, exogenous proteins, which enter the endosomal processing pathway (as in the case of antigens presented by MHC class II molecules), are not effective at generating $CD8^+$CTL responses.

Efforts to generate CTL responses have included the use of replicating vectors to produce the protein antigen within the cell or have focused upon the introduction of peptides into the cytosol. Both of these approaches have limitations that may reduce their utility as vaccines. Retroviral vectors have restrictions on the size and structure of polypeptides that can be expressed as fusion proteins while maintaining the ability of the recombinant virus to replicate, and the effectiveness of vectors such as vaccinia for subsequent immunizations may be compromised by immune responses against the vectors themselves. Also, viral vectors and modified pathogens have inherent risks that may hinder their use in humans. Furthermore, the selection of peptide epitopes to be presented is dependent upon the structure of an individual's MHC antigens and, therefore, peptide vaccines may have limited effectiveness due to the diversity of MHC haplotypes in outbred populations.

Intramuscular inoculation of polynucleotide constructs. i.e., DNA plasmids encoding proteins, have been shown to result in the in situ generation of the protein in muscle cells. By using cDNA plasmids that encode viral proteins, antibody responses that provide homologous protection against subsequent challenge can be generated. The use of polynucleotide vaccines (PNVs) to generate antibodies may result in an increased duration of the antibody responses as well as the provision of an antigen that may have the proper post-translational modifications and conformation of the native protein (vs. a recombinant protein). The viral proteins produced in vivo after PNV immunization may assume their native conformation, thereby eliciting the production of virus neutralizing antibody. The generation of CTL responses by this means offers the benefits of cross-strain protection without the use of a live potentially pathogenic vector or attenuated virus.

Benvenisty et al. reported that $CaCl_2$ precipitated DNA introduced into mice intraperitoneally, intravenously or intramuscularly could be expressed. More recently, intramuscular (i.m.) injection of DNA expression vectors in mice was reported to result in the uptake of DNA by the muscle cells and expression of the protein encoded by the DNA (J. A. Wolff et al., 1990; G. Ascadi et al., 1991). The injected plasmids were shown to be maintained extrachromosomally and did not replicate. Subsequently, persistent expression after i.m. injection in skeletal muscle of rats, fish and primates, and cardiac muscle of rats has been reported. The technique of using nucleic acids as immunogenic agents was reported in WO90/11092 (4 Oct. 1990), in which naked polynucleotides were used to vaccinate vertebrates.

The method is not limited to intramuscular injection. For example, the introduction of gold microprojectiles coated with DNA encoding bovine growth hormone (BGH) into the skin of mice resulted in production of anti-BGH antibodies in the mice. A jet injector has been used to transfect skin, muscle, fat, and mammary tissues of living animals. Various methods for introducing nucleic acids were reviewed by Donnelly, Ulmer and Liu (The Immunologist, 2:20, 1994).

This invention contemplates a variety of methods for introducing nucleic acids into living tissue to induce expression of proteins. This invention provides methods for introducing viral proteins into the antigen processing pathway to generate virus-specific CTLs and antibodies. Thus, the need for specific therapeutic agents capable of eliciting desired prophylactic immune responses against viral pathogens is met for papilloma virus by this invention. Therefore, this invention provides DNA constructs encoding viral proteins of the human papilloma virus which encode induce specific CTLs and antibodies.

The protective efficacy of DNA vaccination against subsequent viral challenge is demonstrated by immunization with non-replicating plasmid DNA encoding one or more of the above mentioned viral proteins. This is advantageous since no infectious agent is involved, no assembly of virus particles is required, and determinant selection is permitted. Furthermore, because the sequence of some of the gene products is conserved among various types of papilloma viruses, protection against subsequent challenge by a different type of papilloma virus that is homologous to or heterologous to the strain from which the cloned gene is obtained is enabled.

SUMMARY OF THE INVENTION

DNA constructs encoding papilloma virus gene products, capable of being expressed upon direct introduction into animal tissues are novel prophylactic and therapeutic pharmaceuticals which can provide immune protection against infection by papilloma virus.

BRIEF DESCRIPTION OF THE DRAWINGS

FIG. 5. Protective responses obtained in rabbits vaccinated with L1 DNA after challenge with CRPV.

DETAILED DESCRIPTION OF THE INVENTION

Figure 1:
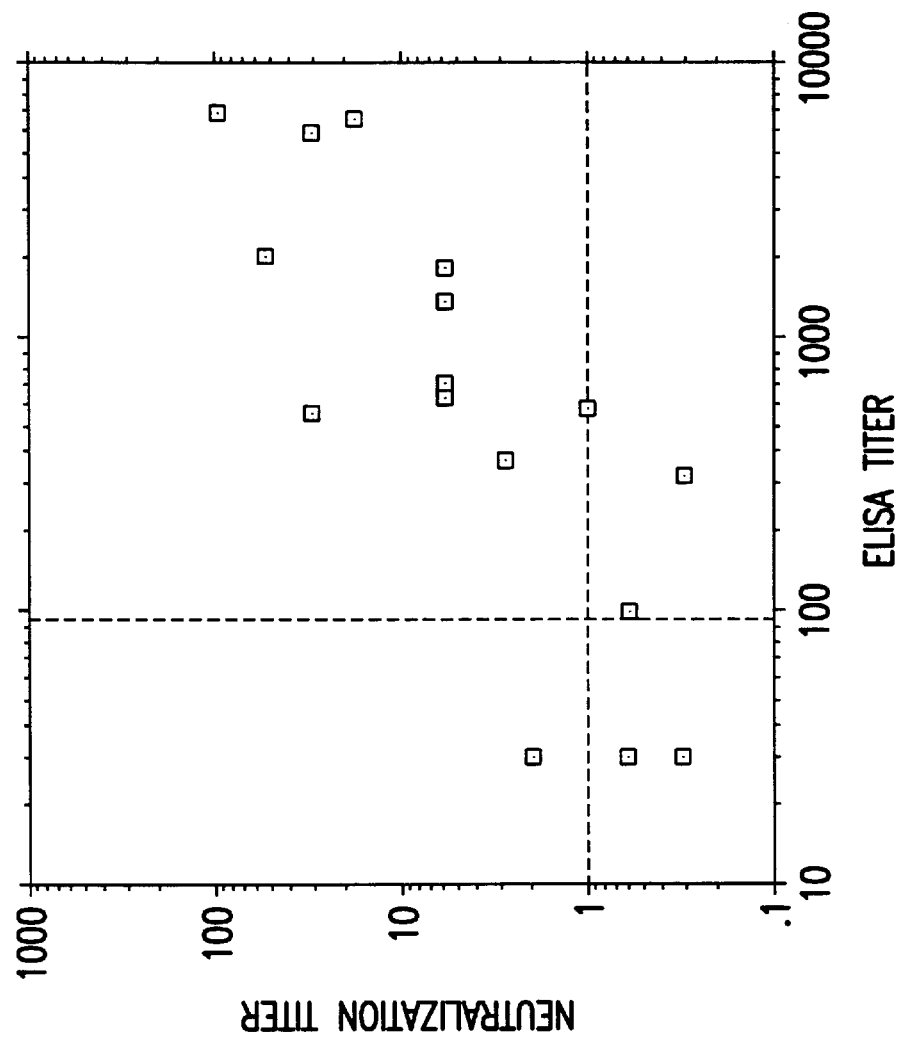
FIG. 1 shows the virus neutralizing antibody response induced in rabbits injected with CRPV L1 DNA, or with a mixture of L1 and L2 DNA (y-axis), and the corresponding ELISA titers induced the same.

DNA constructs encoding papilloma virus gene products, capable of being expressed upon direct introduction into animal tissues are novel prophylactic and therapeutic pharmaceuticals which can provide immune protection against infection by papilloma virus.

This invention provides polynucleotides which, when directly introduced into a vertebrate animal such as cottontail rabbits and humans, induce expression of encoded peptides within the tissues of the animal. Where the peptide is one that does not occur in that animal except during infections, such as proteins associated with papilloma virus (PV), the immune system of the animal is activated to launch a protective response. Because these exogenous proteins are produced by cells of the host animal, they are processed and presented by the major histocompatibility complex (MHC). This recognition is analogous to that which occurs upon actual infection with the related organism. The result, as shown herein, is induction of immune responses which may protect against virulent infection.

As used herein, a polynucleotide is a nucleic acid that contains essential regulatory elements such that upon introduction into a living vertebrate cell, is able to direct cellular machinery to produce translation products encoded by the genes comprising the polynucleotide. There are many embodiments of the instant invention which those skilled in the art can appreciate from the specification. For example, different transcriptional promoters, terminators, carrier vectors or specific gene sequences may be used.

This invention provides nucleic acids which when introduced into animal tissues in vivo induces the expression of the papilloma virus gene product. Thus, for example, injection of DNA constructs of this invention into the muscle of rabbit induces expression of the encoded gene products and elicits virus neutralizing antibodies. Upon subsequent challenge with cottontail rabbit papilloma virus (CRPV), using doses which cause lesions on all control rabbits, animals injected with the polynucleotide vaccine exhibit much reduced lesions. Thus, this invention discloses a vaccine useful in humans to prevent papilloma virus infections.

DNA constructs encoding papilloma viral proteins elicit protective immune responses in animals. As will be described in more detail below, immune responses in animals have included virus neutralizing antibody and protection from viral challenge in rabbits with homologous types of papilloma virus.

In one embodiment, the vaccine product will consist of separate DNA plasmids encoding, for example, the L1, L2, E2, E4 proteins of papilloma virus, either alone or in combination.

Anticipated advantages over other vaccines include but are not limited to increased breadth of protection due to CTL responses, increased breadth of antibody, and increased duration of protection.

In one embodiment of the invention, the L1 or L2 or L1+L2 from HPV type 6a, 6b, 11, 16 or 18 protein sequence, obtained from clinical isolates, is cloned into an expression vector. The vector contains a promoter for RNA polymerase transcription, and a transcriptional terminator at the end of the HPV coding sequence. Examples of promoters include but are not limited to CMV. Examples of transcriptional terminators include but are not limited to BGH. In addition, to assist in preparation of the pharmaceutical, an antibiotic resistance marker expressed in *E. coli* is also preferably included in the expression vector. Neomycin resistance genes or any other pharmaceutically acceptable antibiotic resistance marker may be used. Further, to aid in the high level production of the pharmaceutical by fermentation in prokaryotic organisms, it is advantageous for the vector to contain an origin of replication and be of high copy number. A variety of commercially available prokaryotic cloning vectors provide these benefits. It is desirable to remove non-essential DNA sequences.

Therefore, this invention provides expression vectors encoding a PV protein as an immunogen. The invention offers a means to induce cross-type protective immunity without the need for self-replicating agents. In addition, immunization with DNA offers a number of other advantages. First, this approach to vaccination should be applicable to tumors as well as infectious agents, since the CD8+CTL response is important for immunological intervention in both pathophysiological processes. Therefore, eliciting an immune response against a protein crucial to the transformation process may be an effective means of cancer protection or immunotherapy. Second, the generation of antibodies against expressed proteins after injection of DNA encoding a viral protein suggests that this technology provides a facile and effective means of making antibody-inducing vaccines.

The ease of producing and purifying DNA constructs compares favorably with that of traditional protein purification, which facilitates the generation of combination vaccines. Thus, multiple constructs, for example constructs encoding L1 and L2 proteins of one or more types of HPV, may be prepared, mixed and co-administered. Finally, because protein expression may be maintained for a period of time following DNA injection, the persistence of B- and T-cell memory may be enhanced, thereby engendering long-lived humoral and cell-mediated immunity.

The limitations of proposed HPV vaccines emphasize the need for development of more effective means for prevention of infection and amelioration of disease. Generation of an improved CTL response against a conserved protein may provide significant long-term, cross-reactive immunity.

We have demonstrated protein expression from PNV constructs in rabbits by detection of host immune response directed against CRPV antigens. The results of these animal experiments indicate that direct DNA injection may provide a method for protection of humans against HPV infection and disease.

A range of doses is compared for immunogenicity in order to optimize concentrations for use. It is predictable that dosages of 10, 50, 100, and 200 $\mu$g of DNA are efficacious in man.

Human efficacy is shown in volunteers who receive HPV DNA vaccine. The composition, dosage and administration regimens for the vaccine are based on the foregoing studies. Clinical efficacy is shown by infection rate, illness scores, and duration of illness. These clinical findings are compared with laboratory evaluation of host immune response and viral detection in order to determine surrogate markers which correlate with protection.

Molecular biology for preparing and purifying DNA constructs enable the preparation of the DNA pharmaceuticals of this invention. While standard techniques of molecular biology are sufficient for the production of the products of this invention, the specific constructs disclosed herein provide novel therapeutics which may produce cross-strain protection.

The amount of expressible DNA to be introduced to a vaccine recipient will depend on the strength of the transcriptional and translational promoters used in the DNA construct, and on the immunogenicity of the expressed gene product. In general, an immunologically or prophylactically effective dose of about 1 $\mu$g to 1 mg. and preferably about 10 $\mu$g to 300 $\mu$g is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided.

The polynucleotide may be naked, that is, unassociated with any proteins, adjuvants or other agents which affect the recipient's immune system. In this case, it is desirable for the polynucleotide to be in a physiologically acceptable solution, such as, but not limited to, sterile saline or sterile buffered saline. Alternatively, the polynucleotide may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, viral proteins and other transfection facilitating agents may also be used to advantage. These agents are generally referred to as transfection facilitating agents and as pharmaceutically acceptable carriers.

There are several advantages of immunization with a gene rather than its gene product. One advantage is the relative simplicity with which native or nearly native antigen may be presented to the immune system. Another advantage of polynucleotide immunization is the potential for the immunogen to enter the MHC class I pathway and evoke a cytotoxic T cell response. Since polynucleotide immunization may elicit both humoral and cell-mediated responses, another advantage may be that it provides a relatively simple method to survey a large number of viral genes and viral types for the vaccine potential. Immunization by injection of polynucleotides also allows the assembly of multicomponent vaccines by mixing individual components.

As used herein, the term gene refers to a segment of nucleic acid which encodes a discrete polypeptide. The term pharmaceutical, and vaccine are used interchangeably to indicate compositions useful for inducing immune responses. The terms construct, and plasmid are used interchangeably. The term vector is used to indicate a DNA into which genes may be cloned for use according to the method of this invention.

Accordingly, one embodiment of this invention is a method for using PV genes to induce immune responses in vivo, in a vertebrate such as a mammal, including a human, which comprises:

a) isolating at least one PV gene,
b) linking the gene to regulatory sequences such that the gene is operatively linked to control sequences which, when introduced into a living tissue direct the transcription initiation and subsequent translation of the gene,
c) introducing the gene into a living tissue, and
d) optionally, boosting with additional PV gene.

Another embodiment of this invention may be a method for protecting against heterologous types of PV. This is accomplished by administering an immunologically effective amount of a nucleic acid which encodes a conserved PV epitope.

In another embodiment of this invention, the polynucleotide vaccine encodes another PV protein, such as L1 or L2 or E1 through E7 or combinations thereof.

In another embodiment of this invention, the DNA construct encodes proteins of HPV types 6a, 6b, 11, 16, or 18, wherein the DNA construct is capable of being expressed upon introduction into animal tissues in vivo and inducing an immune response against the expressed product of the encoded HPV gene. Combinations comprising such constructs with polynucleotides encoding other antigens, unrelated to HPV, are contemplated by the instant invention.

Examples of HPV gene encoding DNA constructs include:

V1J-L1, V1J-L2, V1J-E1, V1J-E2, V1J-E3, V1J-E4, V1J-E5, V1J-E6, V1J-E7, V1J-E1iˆE4, V1J-E1ˆE4-L1, V1J-E2-C

In specific embodiments of this invention, the DNA construct encodes CRPV L1 protein, wherein the DNA construct is capable of being expressed upon introduction into animal tissues in vivo and inducing an immune response against the expressed product of the encoded CRPV gene. Combinations comprising such constructs with polynucleotides encoding other antigens, unrelated to CRPV, are contemplated by the instant invention.

Examples of CRPV gene encoding DNA constructs include:

V1J-L1, V1J-L2, V1J-E1, V1J-E2, V1J-E3, V1J-E4, V1J-E5, V1J-E6, V1J-E7, V1J-E1iˆE4, V1J-E1ˆE4-L1, V1J-E2-C.

Pharmaceutically useful compositions comprising the DNA may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the HPV DNA.

Therapeutic or diagnostic compositions of the invention are administered to an individual in amounts sufficient to treat or diagnose PV infections. The effective amount may vary according to a variety of factors such as the individual's condition, weight, sex and age. Other factors include the mode of administration. Generally, the compositions will be administered in dosages ranging from about 1 microgram to about 1 milligram.

The pharmaceutical compositions may be provided to the individual by a variety of routes such as subcutaneous, topical, oral and intramuscular.

The vaccines of the invention comprise HPV DNA that encode recombinant proteins of HPV that contain the antigenic determinants that induce the formation of neutralizing antibodies in the human host. Such vaccines are also safe enough to be administered without danger of clinical infection; do not have toxic side effects; can be administered by an effective route; are stable; and are compatible with vaccine carriers.

The vaccines may be administered by a variety of routes, such as orally, parenterally, subcutaneously or intramuscularly. The dosage administered may vary with the condition, sex, weight, and age of the individual; the route of administration; and the type PV of the vaccine. The vaccine may be used in dosage forms such as capsules, suspensions, elixirs, or liquid solutions. The vaccine may be formulated with an immunologically acceptable carrier.

The vaccines are administered in prophylactically or therapeutically effective amounts, that is, in amounts sufficient to generate a immunologically protective response. The effective amount may vary according to the type of PV. The vaccine may be administered in single or multiple doses.

The methods of the present invention make possible the formulation of monovalent and multivalent vaccines for preventing PV infection. Using the methods, either monovalent or multivalent PV vaccines may be made. For example, a monovalent HPV type 16 vaccine may be made by formulating DNA encoding HPV 16 L1 protein or L2 protein or L1+L2 proteins. Alternatively, a multivalent HPV vaccine may be formulated by mixing DNA encoding HPV L1 or L2 or L1+L2 proteins from different HPV types.

The DNA may be used to generate antibodies. The term "antibody" as used herein includes both polyclonal and monoclonal antibodies, as well as fragments thereof, such as, Fv, Fab and F(ab)2 fragments that are capable of binding antigen or hapten.

The PV DNA and antibodies of the present invention may be used to serotype HPV or CRPV infection and for HPV screening. The HPV and CRPV DNA and antibodies lend themselves to the formulation of kits suitable for the detection and serotyping of HPV or CRPV. Such a kit would comprise a compartmentalized carrier suitable to hold in close confinement at least one container. The carrier would further comprise reagents such as HPV DNA or anti-HPV antibodies suitable for detecting a variety of HPV types. The carrier may also contain means for detection such as labeled antigen or enzyme substrates or the like.

The following examples are provided to further define the invention without, however, limiting the invention to the particulars of these examples.

EXAMPLE 1

VECTORS FOR VACCINE PRODUCTION

A) V1: The expression vector V1 was constructed from pCMVIE-AKI-DHFR [Y. Whang et al., J. Virol. 61, 1796 (1987)]. The AKI and DHFR genes were removed by cutting the vector with EcoR I and self-ligating. This vector does not contain intron A in the CMV promoter, so it was added as a PCR fragment that had a deleted internal Sac I site [at 1855 as numbered in B. S. Chapman et al., Nuc. Acids Res. 19, 3979 (1991)]. The template used for the PCR reactions was pCMVintA-Lux, made by ligating the Hind III and Nhe I fragment from pCMV6a120 [see B. S. Chapman et al., ibid.,] which includes hCMV-IE1 enhancer/promoter and intron A, into the Hind III and Xba I sites of pBL3 to generate pCMVIntBL. The 1881 base pair luciferase gene fragment (Hind III-Sma I Klenow filled-in) from RSV-Lux [J. R. de Wet et al., Mol. Cell Biol. 7, 725, 1987] was cloned into the Sal I site of pCMVIntBL, which was Klenow filled-in and phosphatase treated.

The primers that spanned intron A are:

5' primer, 5'-CTATATAAGCAGAGCTCGTTTAG-3'; (SEQ ID NO: 1)

3' primer, 5'-GTAGCAAAGATCTAAGGACGGTGACTGCAG-3'; (SEQ ID NO: 2)

The primers used to remove the Sac I site are:

Sense primer, SEQ ID: 3:
5-GTATGTGTCTGAAAATGAGCGTGGAGATTGGGCTCGCAC-3';

and antisense primer, SEQ ID: 4:,
5'-GTGCGAGCCCAATCTCCACGCTCATTTTCAGACACATAC-3'.

The PCR fragment was cut with Sac I and Bgl II and inserted into the vector which had been cut with the same enzymes.

B) V1J EXPRESSION VECTOR

Our purpose in creating V1J was to remove the promoter and transcription termination elements from our vector, V1, in order to place them within a more defined context, create a more compact vector, and to improve plasmid purification yields.

V1J is derived from vectors V1 and pUC19, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes was purified from an agarose electrophoresis gel. The ends of this DNA fragment were then "blunted" using the T4 DNA polymerase enzyme in order to facilitate its ligation to another "blunt-ended" DNA fragment.

pUC19 was chosen to provide the "backbone" of the expression vector. It is known to produce high yields of plasmid, is well-characterized by sequence and function, and is of minimum size. We removed the entire lac operon from this vector, which was unnecessary for our purposes and may be detrimental to plasmid yields and heterologous gene expression, by partial digestion with the HaeII restriction enzyme. The remaining plasmid was purified from an agarose electrophoresis gel, blunt-ended with the T4 DNA polymerase, treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in E. coli and was designated V 1J. This vector's structure was verified by sequence analysis of the junction regions and was subsequently demonstrated to give comparable or higher expression of heterologous genes compared with V1.

C) V1Jneo EXPRESSION VECTOR

It was necessary to remove the $amp^r$ gene used for antibiotic selection of bacteria harboring V1J because ampicillin may not be used in large-scale fermenters for the production of human clinical products. The $amp^r$ gene from the pUC backbone of V1J was removed by digestion with SspI and Eam1105I restriction enzymes. The remaining plasmid was purified by agarose gel electrophoresis, blunt-ended with T4 DNA polymerase, and then treated with calf intestinal alkaline phosphatase. The commercially available $kan^r$ gene, derived from transposon 903 and contained within the pUC4K plasmid, was excised using the PstI restriction enzyme, purified by agarose gel electrophoresis, and blunt-ended with T4 DNA polymerase. This fragment was ligated with the V1J backbone and plasmids with the $kan^r$ gene in either orientation were derived which were designated as V1Jneo #'s 1 and 3. Each of these plasmids was confirmed by restriction enzyme digestion analysis, DNA sequencing of the junction regions, and was shown to produce similar quantities of plasmid as V1J. Expression of heterologous gene products was also comparable to V1J for these V1Jneo vectors. We arbitrarily selected V1Jneo#3, referred to as V1Jneo hereafter, which contains the $kan^r$ gene in the same orientation as the $amp^r$ gene in V1J as the expression construct.

D) V1Jns EXPRESSION VECTOR:

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

EXAMPLE 2

Preparation Of DNA Constructs Encoding Cottontail Rabbit Papilloma Virus Proteins The source of the CRPV DNA for all cloned genes is CRPV-pLAII. This is the entire CRPV genome cloned into pBR322 at the Sal I site (Nasseri, M., Meyers, C. and Wettstein, F. O. (1989) Genetic analysis of CRPV pathogenesis: The L1 open reading frame is dispensable for cellular transformation but is required for papilloma formation, Virology 170, 321–325).

1. V1Jns-L1: The L1 coding sequence was generated by PCR, using the CRPV-pLAII DNA as template. The PCR primers were designed to contain Bam HI sites for cleavage after the PCR fragment was gel purified.

The primers used to generate the L1 coding region were:

Sense Primer:
5'GGTACAGGAT CCACCATGGC AGTGTGGCTG
TCTACGCAG 3'(SEQ ID NO: 5)         BamHI -continued Anti-sense Primer:
5'CCACATGGAT CCTTAAGTAC GTCTCTTGCG
TTTAGATG 3'(SEQ ID NO: 6)   BamHI The PCR fragment was gel purified, cut with Bam HI and ligated to V1Jns cut with Bgl II.

2. V1Jns-L2: The L2 coding region was generated by PCR. The vector CRPV-pLAII has the L2 gene disrupted by the Sal I site used in inserting CRPV into pBR322. Therefore, a template for PCR was generated by cutting CRPV-pLAII with SalI and ligating the CRPV DNA into circular form at the SAl I site. This ligated CRPV DNA was used as the template for PCR. The PCR primers were designed to contain Bam HI sites for cleavage after the PCR fragment was gel purified.

The primers used to generate the L2 coding region were:

Sense Primer:
5'GGTACAGGAT CCACCATGGT TGCACGGTCA
CGAAAACGC 3'(SEQ ID NO: 7)   BamHI Anti-sense Primer:
5'CCACATGGAT CCTTATTCTG CGTAGACAGC CACACT 3'
(SEQ ID NO: 8)   BamHI 3. V1Jns-E2: The E2 coding region is generated by PCR, using the CRPV-pLAII DNA as template. The PCR primers are designed to contain Bgl II sites for cleavage after the PCR fragment is gel purified.

The primers used to generate the E2 coding region are:

Sense Primer:
5'GGTACAAGAT CTACCATGGA GGCTCTCAGC
CAGCGCTTA 3'(SEQ ID NO: 9)   BglII Anti-sense Primer:
5'CCACATAGAT CTCTAAAGCC CATAAAAATT
CCCTAAAAAC AC 3'(SEQ ID NO: 10) BglII 4. V1Jns-E4: The E4 coding region is generated by PCR, using the CRPV-pLAII DNA as template. The PCR primers are designed to contain Bgl II sites for cleavage after the PCR fragment is gel purified.

The primers used to generate the E4 coding region are:

Sense Primer:
5'GGTACAAGAT CTACCATGAG CCATGGACAT
TGCAGGATAC 3'(SEQ ID NO: 11) BglII Anti-sense Primer:
5'CCACATAGAT CTTTATAAGC TCGCGAAGCC
GTCTATTCC 3'(SEQ ID NO: 12)   BglII 5. V1Jns-E7: The E7 coding region was generated by PCR, using the CRPV-pLAII as template in one case and purified DNA from Kreider's CRPV strain in another case. The same PCR primers were used for both templates. The PCR primers are designed to contain Bgl II sites for cleavage after the PCR fragment was gel purified.

The primers used to generate the E7 coding region were:

Sense Primer:
5'GGTACAAGAT CTACCATGAT AGGCAGAACT
CCTAAGCTTA G 3'(SEQ ID NO: 13)
BglII Anti-sense Primer:
5'CCACATAGAT CTTCAGTTAC AACACTCCGG
GCACAC 3'(SEQ ID NO: 14)

6. pGEX-2T-E2: The E2 coding region was generated by PCR as described for V1Jns-E2. The fragment was cloned into pGEX-2T into the Bam HI site to generate an in-frame fusion to glutathione S-transferase (GST). This construct is used to generate protein in E. coli.

7. pGEX-2T-E4: The E4 coding region was generated by PCR as described for V1Jns-E4. The fragment was cloned into pGEX-2T into the Barn HI site to generate an in-frame fusion to glutathione S-transferase (GST). This construct is used to generate protein in E. coli.

8. pGEX-2T-E7: The E7 coding region was generated by PCR as described for V1Jns-E7. The fragment was cloned into pGEX-2T into the Bam HI site to generate an in-frame fusion to glutathione S-transferase (GST). This construct is used to generate protein in E. coli.

EXAMPLE 3
Plasmid Purification from E. coli

V1J constructs were grown overnight to saturation. Cells were harvested and lysed by a modification of an alkaline SDS procedure (Sambrook, J., Fritsch, E. F., And Maniatis, T., Molecular Cloning: A Laboratory Manual. Cold Spring Harbor Laboratory Press. Cold Spring Harbor, N.Y., ed.2 (1989). The modification consisted of increasing the volumes three-fold for cell lysis and DNA extraction. DNA was purified by double banding on CsCl-EtBr gradients. The ethidium bromide was removed by 1-butanol extraction. The resulting DNA was extracted with phenol/chloroform and precipitated with ethanol. DNA was resuspended in TE (10 mM Tris, 1 mM EDTA), pH 8 for transfections and in 0.9% NaCl for injection into mice. Concentration and purity of each DNA preparation was determined by $OD_{260/280}$ readings. The 260/280 ratios were $\geq 1.8$.

EXAMPLE 4
Production of CRPV Specific Antibodies In Vivo

Five rabbits per group were bled and then injected with 1.2 ml of saline containing 1 mg of V1Jns-L1, V1Jns-L2, V1Jns-L1 mixed with V1Jns-L2 (2 mg total), or with V1Jns (control vector with no protein encoded) alone. The inoculum was divided equally among six intramuscular sites on both hind legs, both forelegs, and the lower back. Three weeks after the initial DNA injection, the rabbits were bled and given a second injection of the same DNA in the same manner. Four weeks after the second injection, the animals were bled again.

Sera were tested for virus neutralizing antibody by mixing tenfold serial dilutions of immune serum with a 1:3 dilution of CRPV stock virus (Kreider strain). Dilutions were prepared in Dulbecco's Modified Eagle's Medium (DMEM) supplemented with 1% bovine serum albumin (BSA). CRPV stock virus (purchased from Dr. J. Kreider, Hershey, Pa.) was prepared from skin fragments obtained from wild cottontail rabbits, which were infected with CRPV and implanted under the renal capsules of athymic mice. The resulting condylomas were homogenized and clarified by centrifugation to yield a stock virus preparation. The mixtures of immune serum and virus stock were incubated on ice for at least 60 minutes, and then 50 µl of each mixture was applied to a 1 $cm^2$ area of shaved, scarified skin on the backs of 3 New Zealand White rabbits. The animals were observed 7 weeks later for the presence of warts and the anteroposterior and lateral dimensions (in mm) of the ellipsoidal warts were measured. Endpoint titers were determined from the frequency of warts at the various dilutions by Reed-Muench interpolation. Neutralizing antibody titers of rabbits injected with L1 DNA or both L1 and L2 DNA are plotted on the y-axis of FIG. 1.

Figure 2:
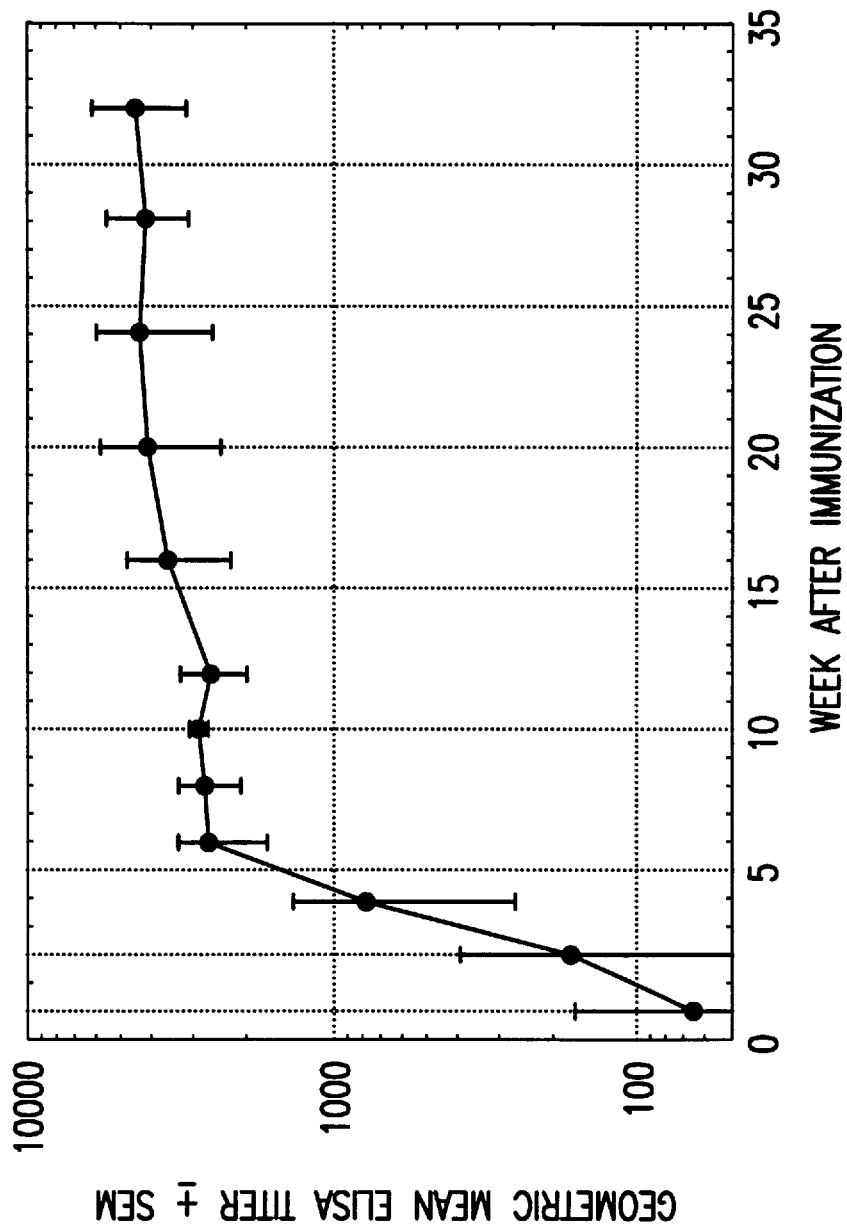
FIG. 2. Antibody responses of rabbits injected with L1 DNA. ELISA titers against L1 VLP of rabbits given a single immunization with an arbitrarily selected dosage of 1 mg of L1 DNA are shown. Rabbits injected with control DNA did not produce detectable antibodies against L1 VLP.

The sera from rabbits that had been injected with L1 DNA also were tested for antibody by ELISA. Polystyrene ELISA plates were coated overnight at 4° C. with 1 μg/well of semipurified, recombinant yeast-derived CRPV L1 protein. The recombinant L1 was prepared in *S. cerevisiae* and purified as described by Kirnbauer et al. (Proc. Nat. Acad. Sci. U.S.A. 89:12180–4, 1992) with minor modifications. Diluted sera were added and incubated for 1 hour at room temperature (with shaking on an orbital shaker). The plates were then washed and horseradish peroxidase-labeled goat anti-rabbit IgG (Fc specific) was added. After one hour of incubation with shaking the plates were washed and substrate was added. Plates were read at 450 nm using a kinetic ELISA reader (Molecular Devices Corp.), and the values obtained were corrected for background by subtraction of the reaction rate of the preimmune serum from that of the postimmnunization serum at the same dilution. Titers were determined by interpolation of the resulting curve of corrected reaction rate versus dilution to a rate value of 10 mOD/min. ELISA titers of rabbits injected with L1 DNA or L1 plus L2 DNA are plotted on the x-axis of FIG. 1. FIG. 1 shows that 12/13 sera that were positive for neutralizing activity (log titer≧1, i.e., positive with undiluted serum) also were positive for ELISA antibody (ELISA titer≧100). Four of the 4 sera that were negative for neutralizing antibody had ELISA titers≦350. All of the sera from rabbits that received either L2 DNA alone or the V1J control vector had ELISA titers of less than 100. Taken together, these data show that antibodies specific for CRPV and capable of neutralizing it were obtained after injection of L1 DNA. ELISA titers in rabbits persisted undiminished for at least 32 weeks following immunization (FIG. 2).

EXAMPLE 5

Protection of Rabbits upon Challenge with Virulent CRPV

Five rabbits per group were injected intramuscularly with 1 mg, of V1Jns-L1, V1Jns-L2, V1Jns-L1 mixed with V1Jns-L2 (2 mg total), or with V1Jns (control vector with no protein encoded) alone, as described above. Three weeks after the initial DNA injection, the rabbits received a second injection of the same DNA. Four weeks after the second injection, the rabbits were challenged with CRPV. The CRPV challenge was performed by applying 50 μl of two dilutions of virus stock (diluted 1:2 or 1:12 with DMEM plus 1% BSA) to triplicate 1 cm² sites of shaved, scarified skin on the back of each rabbit. Sera taken at the time of challenge from animals injected with L1 DNA or L1+L2 DNA contained antibody to L1 by ELISA and virus neutralizing antibody as described above. The animals were observed for formation of warts at 3, 6 and 10 weeks following challenge. Of the rabbits that did not receive L1 DNA, 51 of 54 sites challenged with CRPV developed warts, while on animals that received L1 DNA, 2 of 60 sites developed warts. One of the two warts that was observed on a rabbit immunized with L1 DNA regressed within 3 weeks after its appearance. Table 1 shows the distribution of warts on rabbits after CRPV challenge. Prophylactic immunization with L1 DNA protected rabbits from the development of warts upon infection with virulent CRPV.

EXAMPLE 6

Conformational specificify of antibodies induced with L1 DNA

Figure 3B:
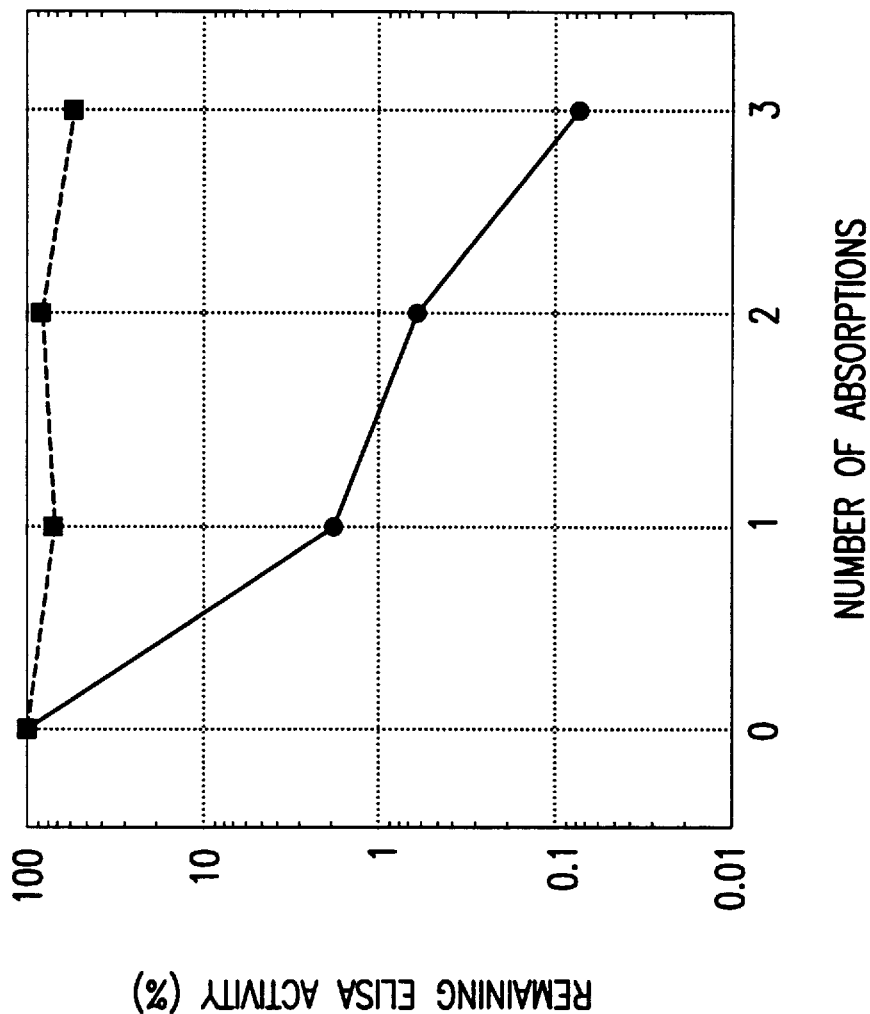
FIGS. 3(A–B). Effect of absorption with L1 VLP on antiserum obtained by immunization with L1 DNA. A, Normal serum, and immune serum absorbed with native or denatured VLPs as in (15), were tested for virus neutralizing activity. The mean areas of condylomas on 3 challenge sites, measured 7 weeks after challenge, are shown. B, Immune serum from a rabbit that had been injected with L1 DNA was serially absorbed three times with native (circles) or denatured (squares) L1 VLP expressed in a recombinant yeast (*Saccharomyces cerevisiae*) strain. After each serial absorption, aliquots of serum then were assayed for antibody activity against baculovirus-derived L1 VLP by ELISA. The ELISA titer of the absorbed material is plotted as a percentage of the original ELISA titer of unabsorbed serum.

To demonstrate that protective neutralizing antibodies recognize conformational epitopes on VLPs, absorption experiments were performed. Absorption of immune serum with L1 VLP (15) removed all of the neutralizing antibody and ELISA activity (FIG. 3A, B). The application to scarified skin of CRPV mixed with preimmune rabbit serum resulted in condylomas on all sites challenged, while when CRPV was mixed with immune serum and similarly applied, no condylomas were seen due to the neutralizing antibody activity. When CRPV was mixed with immune serum that had been absorbed with L1 VLPs, from which the neutralizing antibodies should have been removed, all (3/3) sites were positive for condylomas. In contrast, when immune serum was absorbed with denatured nonparticulate L1 protein (denatured by reduction and alkylation in 8M urea), the serum was still able to neutralize CRPV (FIG. 3A), and retained its activity in the ELISA (FIG. 3B). Thus the virus-neutralizing antibodies induced by L1 DNA immunization could be removed only by L1 VLPs in a native conformation and not by denatured L1. The ELISA assay appears to detect primarily conformationally-specific antibodies reacting with intact L1 VLP, as the depletion of ELISA activity by absorption corresponded to the removal of neutralizing antibodies (FIG. 3B).

EXAMPLE 7

Antibody responses induced with E2 and E7 DNA

Figure 4A:
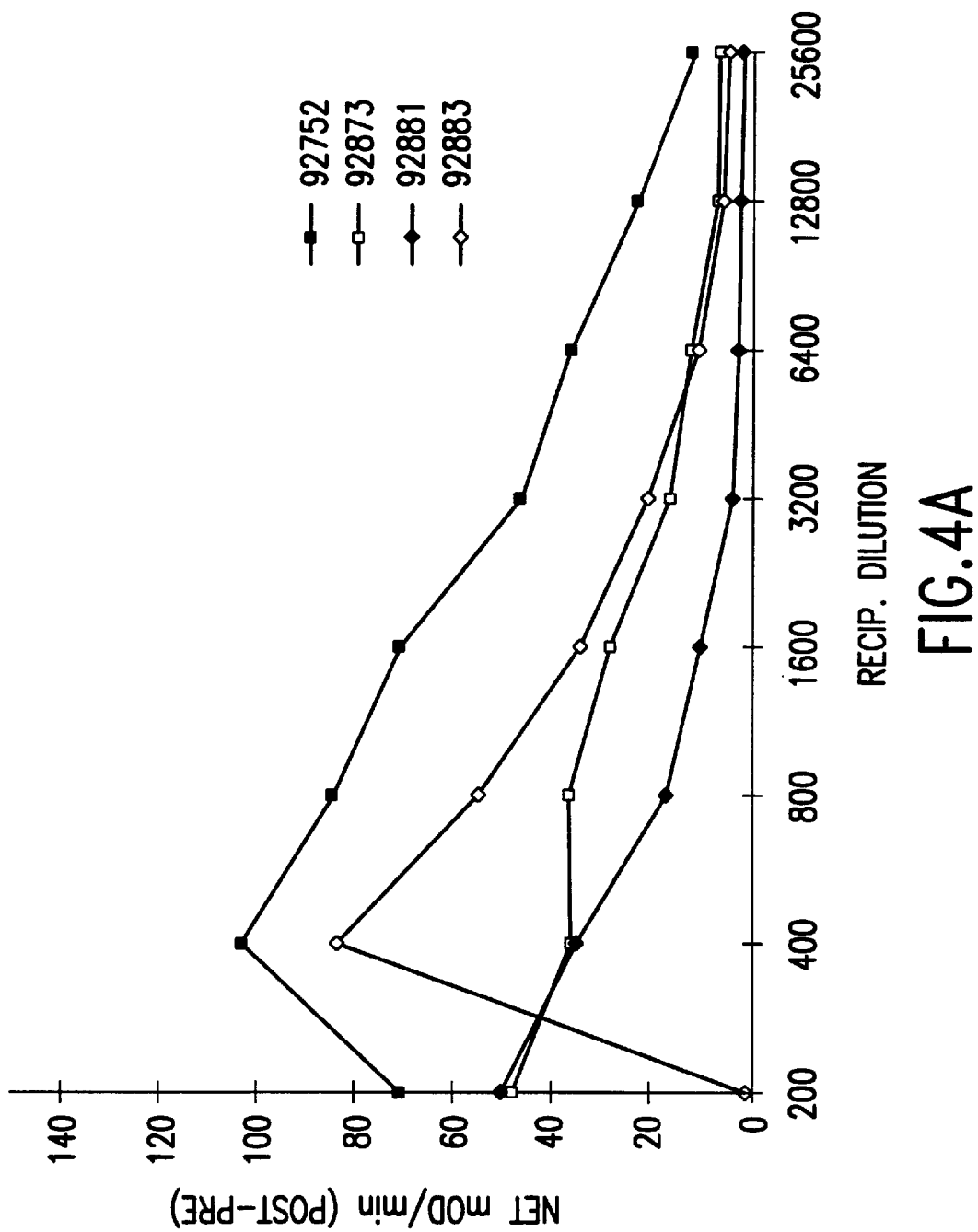
FIGS. 4(A–B). ELISA responses in assays for anti-CRPV E2 (A) and CRPV E7 (b) antibodies. The net reaction rate (rate for post dose 4 minus rate for preimmune at the same dilution) in mOD/min is shown for each individual rabbit.

Groups of 4 NZW rabbits were injected intramuscularly with 1 mg of V1J-E2 or V1J-E7 DNA per immunization. Four immunizations were given at 0, 4, 9 and 20 weeks and were bled at 22 weeks. Antibodies were used as surrogate markers for expression of the encoded proteins. Serum antibodies were assayed using ELISA plates (NUNC Maxisorp) coated with 1 μg per well of GST-E2 or GST-E7 fusion protein purified from *E. coli* that had been transformed with a pGEX expression vector encoding CRPV E2 or E7 and induced with IPTG. The ELISA assay was performed as described in Example 3. The net reaction rated (post dose 4 minus preimmune) in mOD/min are shown in FIG. 4. Net rates>10 mOD/min are considered positive; specimens with high antibody titers may have low net reaction rates at the lowest dilution due to oversaturation of the detection system. Thus the encoded E2 and E7 proteins were expressed and recognized by the recipient immune system.

What is claimed is:

1. A papillomavirus (PV) vaccine for use in a human comprising a vector comprising:
   (a) a polynucleotide encoding at least one human papillomavirus (HPV) gene from an HPV selected from the group consisting of: HPV 6a, HPV 6b, HPV 11, HPV 16 and HPV 18, and expressing a protein selected from the group consisting of: L1 and L1+L2,
   (b) a CMV promoter for RNA polymerase transcription;
   (c) a transcriptional terminator from a bovine growth hormone gene; and
   (d) a neomycin resistance marker gene;
wherein the vector is present in a physiologically acceptable solution.

2. A vaccine according to claim 1 wherein the vector is V1Jneo or V1Jns.

3. A method for inducing an immune response to HPV in vivo comprising introducing into a living tissue of a human an HPV vaccine wherein said vaccine comprises a vector comprising:
   (a) a polynucleotide encoding at least one HPV L1 gene from an HPV virus selected from the group consisting of HPV 6a, HPV 6b, HPV 11, HPV 16, and HPV 18;
   (b) a CMV promoter for RNA polymerase transcription;
   (c) a bovine growth hormone transcriptional terminator; and
   (d) a neomycin resistance marker gene;

wherein the vector is present in a physiologically acceptable solution and wherein said L1 gene is expressed and an immune response is induced.

4. A method according to claim 3 wherein the vector is V1Jneo or V1Jns.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

CTATATAAGC AGAGCTCGTT TAG        23

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GTAGCAAAGA TCTAAGGACG GTGACTGCAG        30

( 2 ) INFORMATION FOR SEQ ID NO:3:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

GTATGTGTCT GAAAATGAGC GTGGAGATTG GGCTCGCAC        39

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

GTGCGAGCCC AATCTCCACG CTCATTTTCA GACACATAC        39

( 2 ) INFORMATION FOR SEQ ID NO:5:

( i ) SEQUENCE CHARACTERISTICS:
        ( A ) LENGTH: 39 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

GGTACAGGAT CCACCATGGC AGTGTGGCTG TCTACGCAG    39

( 2 ) INFORMATION FOR SEQ ID NO:6:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:6:

CCACATGGAT CCTTAAGTAC GTCTCTTGCG TTTAGATG    38

( 2 ) INFORMATION FOR SEQ ID NO:7:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GGTACAGGAT CCACCATGGT TGCACGGTCA CGAAAACGC    39

( 2 ) INFORMATION FOR SEQ ID NO:8:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:8:

CCACATGGAT CCTTATTCTG CGTAGACAGC CACACT    36

( 2 ) INFORMATION FOR SEQ ID NO:9:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GGTACAAGAT CTACCATGGA GGCTCTCAGC CAGCGCTTA         39

( 2 ) INFORMATION FOR SEQ ID NO:10:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

CCACATAGAT CTCTAAAGCC CATAAAAATT CCCTAAAAAC AC     42

( 2 ) INFORMATION FOR SEQ ID NO:11:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

GGTACAAGAT CTACCATGAG CCATGGACAT TGCAGGATAC        40

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

CCACATAGAT CTTTATAAGC TCGCGAAGCC GTCTATTCC         39

( 2 ) INFORMATION FOR SEQ ID NO:13:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO -continued ( i v ) ANTI-SENSE: NO ( x i ) SEQUENCE DESCRIPTION: SEQ ID NO:13:

GGTACAAGAT CTACCATGAT AGGCAGAACT CCTAAGCTTA G    41

( 2 ) INFORMATION FOR SEQ ID NO:14:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:14:

CCACATAGAT CTTCAGTTAC AACACTCCGG GCACAC    36